United States Patent [19]
James

[11] 3,991,434
[45] Nov. 16, 1976

[54] BALL CASTOR

[75] Inventor: Michael Joseph James, Cheltenham, England

[73] Assignee: Global Castors and Hardware Limited, England

[22] Filed: July 22, 1975

[21] Appl. No.: 598,160

[30] Foreign Application Priority Data

Aug. 8, 1974 United Kingdom............... 34907/74

[52] U.S. Cl. ................................................. 16/18 A
[51] Int. Cl.² ......................................... B60B 33/08
[58] Field of Search ..................................... 16/18 A

[56] References Cited
UNITED STATES PATENTS

| 3,054,135 | 9/1962 | Shepherd | 16/18 A |
| 3,075,232 | 1/1963 | Rice et al. | 16/18 A |
| 3,177,516 | 4/1965 | Price et al. | 16/18 A |

FOREIGN PATENTS OR APPLICATIONS

| 932,770 | 7/1963 | United Kingdom | 16/18 A |

Primary Examiner—Werner H. Schroeder
Assistant Examiner—Conrad L. Berman
Attorney, Agent, or Firm—Cushman, Darby & Cushman

[57] ABSTRACT

A castor has a domed wheel rotatably mounted about an inclined axis on a body itself pivotally mounted on or about a vertical mounting spindle. The wheel axis is offset laterally of the spindle axis and the wheel has a rim with a convex part-spherical ground-engaging surface. The body is moulded with an integral bearing boss and the wheel is moulded with an integral bearing boss, the bosses engaging one within the other to provide a bearing for the wheel. The spindle is located in a bore in the body and engages in a peripheral groove in the boss to locate the wheel axially with respect to the body. A sleeve-like portion of the body moulding concentric with and surrounding the boss provides an outer female bearing surface for the wheel boss.

11 Claims, 6 Drawing Figures

BALL CASTOR

BACKGROUND OF THE INVENTION

This invention relates to castors of the type commonly referred to as "ball" castors, which have a domed wheel rotatably mounted about an inclined axis on a body itself pivotally mounted on or about a vertical mounting spindle. The wheel axis is off-set laterally of the spindle axis and the wheel has a rim with a convex, generally part-spherical, ground-engaging surface.

The assembly of such castors tends to be labour intensive requiring the fitting of various fixing devices, such as spring rings or the like, which fix the rotatable wheel to the body and locate the spindle. The object of the invention is to provide a castor assembly which is relatively simple to assemble and which, in particular, includes a lesser number of parts than usual and hence can be manufactured comparatively cheaply.

SUMMARY OF THE INVENTION

According to the invention, a castor of the type concerned comprises a moulded body with an integral bearing boss, a rotatably mounted wheel with an integral bearing boss having an external peripheral groove, said bearing bosses engaging one within the other to provide a bearing for the wheel, and a mounting spindle located in a bore in the body and which engages in said groove to locate the wheel axially with respect to the body.

It is preferred that the body boss should act as a stub axle and hence engage within the wheel boss, which is hollow for the purpose, to provide a bearing journal for the wheel. The external periphery of the wheel boss may additionally, or alternatively, provide a bearing journal which runs within a female bearing surface of the body. For economy of moulding material, this female bearing surface may be formed in a sleeve-like portion of the body moulding concentric with and surrounding the body boss. This sleeve-like portion may be thin-walled and interconnected with the surrounding main body portion by a ring of spaced radial strengthening webs.

Preferably, the body and the wheel are both plastics injection mouldings, and to simplify the moulding technique, the wheel boss may be moulded with a plain periphery in which said groove is machined before assembly of the castor. The spindle and the body may have interengaging formations, so that the spindle "snaps-in" to the body and is then retained without the provision of additional fixing means. In a preferred embodiment, the assembly includes a flanged fixing ferrule, in which the spindle is rotatably supported, and a similar snap-in fixing may be employed between the spindle and the ferrule. Thus, an assembly results which consists only of four functionally essential parts, no special fixing components being required.

It is preferred that if provided the fixing ferrule, or other fixing member for attachment to the body to be supported by the castor, should turn freely on the spindle and transmit the vertical load directly to the body for which purpose it may engage a thrust face surrounding the spindle on the body. However, it may be desired to fix the spindle itself directly into the supported body and to this end the spindle preferably also turns freely in the castor body. All the parts, other than the spindle, are conveniently moulded from a plastics material such as nylon. The spindle may be a length of steel rod with two spaced peripheral grooves for snap-in engagement, respectively, with projections in the body and the ferrule or other fixing member. The inner end of the spindle may engage an internal stop face within the body to limit the spindle insertion during assembly of the castor and/or support the load when spindle fixing of the castor is employed.

Other objects and features of the present invention will appear more fully below from the following detailed description considered in connection with the accompanying drawings which disclose one preferred embodiment of the invention. It is to be expressly understood, however, that the drawings are designed for purposes of illustration only and not as a definition of the limits of the invention, reference for the latter purpose being had to the appended claims.

DESCRIPTION OF THE PREFERRED EMBODIMENT

Figure 1:
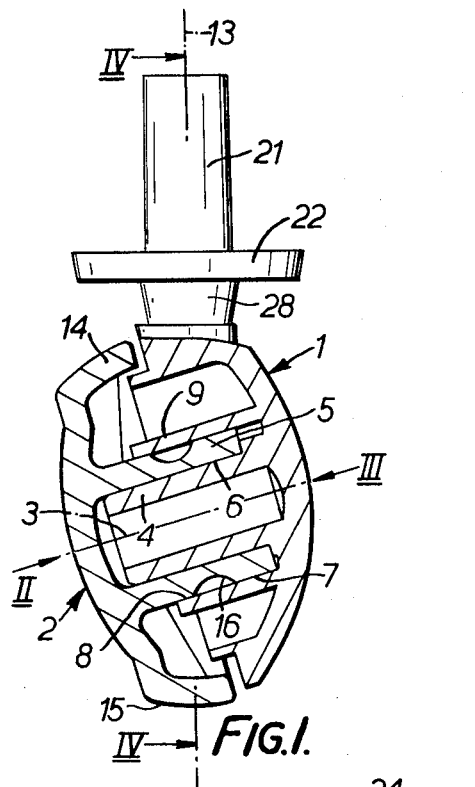
FIG. 1 is a sectional view of a right-hand castor assembly, taken in an axial plane of the castor wheel.
Figure 2:
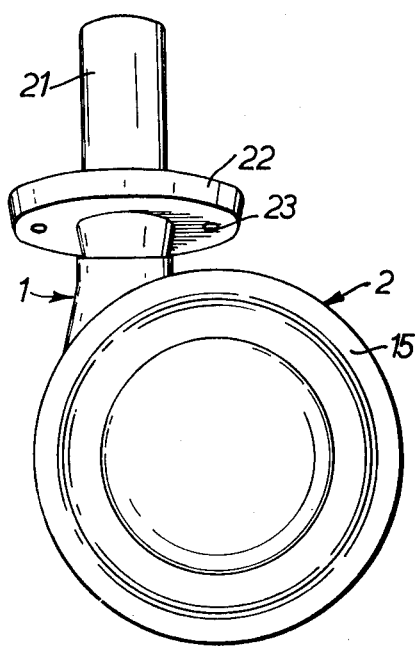
FIG. 2 is an external view of the assembly in the direction of the arrow II in FIG. 1.
Figure 3:
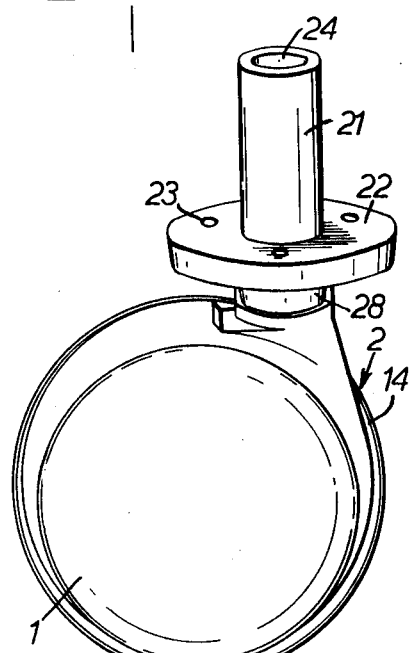
FIG. 3 is an external view in the direction of the arrow III in FIG. 1.
Figure 4:
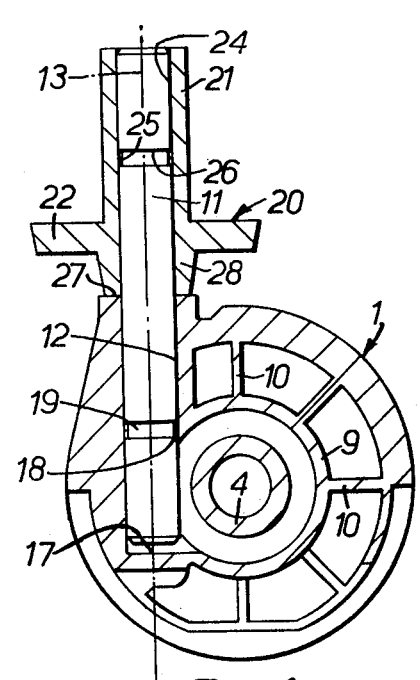
FIG. 4 is a sectional view on the line IV — IV in FIG. 1, with the wheel omitted.
Figure 5:
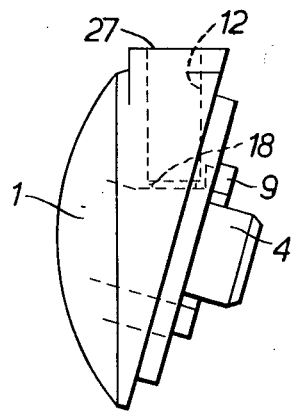
FIGS. 5 and 6 are detail views of a body of the assembly.
Figure 6:
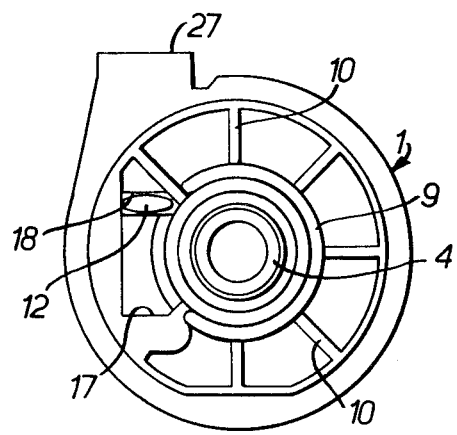

The ball castor illustrated has a dished moulded nylon body 1 on which a domed nylon wheel 2 is rotatably mounted about an axis 3 which, when the castor is fitted and as illustrated, is inclined downwardly away from the body 1 and disposed in a vertical plane. The body 1 is moulded with an internal integral bearing boss acting as a stub axle 4 and which, for material economy, is of hollow tubular form. The wheel 2 has an integral central hollow bearing boss 5, with a cylindrical central bore 6 which runs on the stub axle 4.

For increased bearing strength and rigidity the external periphery 7 of the wheel boss 5 also provides a bearing journal, which runs within a female bearing surface 8 of the body 1. This surface 8 is formed in a sleeve-like portion 9 of the body moulding which is concentric with and surrounds the stub shaft 4. The thin-walled portion 9 is interconnected with the surrounding main portion of the body 1 by a ring of spaced radially-disposed strengthening webs 10.

A top mounting spindle 11 is located in a bore 12 of the body 1. When the castor is fitted the spindle 11 is as shown disposed vertically, and to provide the castor action the spindle axis 13 is offset to one side of the aforesaid vertical plane which contains the axis 3. As viewed at right angles to that plane, as can be seen from FIG. 1, the axis 13 is substantially aligned with the ground-contact point of the rim 14 of the castor wheel 2. The rim 14 has the usual part-spherical convex ground-engaging surface 15, the offsetting of the axes 3 and 13 resulting in the axis 13 in fact intersecting the ground to one side of said vertical plane a corresponding distance from said ground-contact point.

In addition to defining the vertical pivotal axis 13 of the fitted castor, the spindle 11 locates the wheel 2 axially relatively to the body 1 on the axle 4. To this end the spindle 11 engages an annular groove 16 machined in the outer periphery 7 of the wheel boss 5. The cross-sectional shape of the groove is chosen to allow free wheel rotation and to suit the diameter of the spindle 11 and the relative skew angle of the axes 3 and 13.

An internal stop face 17 moulded within the body 1 provides positive axial limitation of insertion of the spindle 11 on assembly, the spindle being pushed into the bore 12 after the wheel and body have been fitted together. Retention of the spindle 11 is achieved by a continuous annular projecting lip 18 moulded in the body 1 within the bore 12 where the latter breaks into the hollow central space of the body between the sleeve portion 9 and the stub axle 4. The wall of this hollow space, which space is open on the side adjacent the wheel 2, provides the spindle stop face 17. The lip 18 resiliently engages a peripheral groove 19 in the spindle 11, so that the latter has a snap-in fitting within the body 1 while being freely rotatable therein.

The castor assembly illustrated includes a ferrule 20 as the chosen type of fixing member, although it will be appreciated that other forms of fixing member may be employed or the fixing member omitted and the spindle itself fixed. The ferrule 20 has a tubular spigot-fixing portion 21 with a fixing flange 22 having screw-fixing holes 23. The spindle 11 turns freely in a bore 24 in the ferrule, the bore 24 being moulded with internal "pips" 25 which engage a second annular groove 26 in the spindle 11. These pips 25 thus provide snap-in location for the spindle 11 in the ferrule 20 also, and thus the castor has the minimum number of functional parts essential to castor operation without any additional fixing elements being required for either the wheel 2 or the spindle 11.

The vertical weight of the body supported is in use transmitted directly to the body 1 of the castor by the ferrule 20, and not through the spindle 11. The body 1 is accordingly moulded with a flat thrust face 27 surrounding the bore 12, this face being engaged by the lower tubular end 28 of the ferrule 20, which is also a nylon moulding.

As already mentioned, if desired, the ferrule 20 or other fixing member can be omitted and the spindle 11 fixed directly into a bore in the article to be supported. When direct spindle fixing in this manner is employed, the stop face 17 within the castor body becomes a thrust face which takes the load applied to the spindle. To allow spindle fixing the retained spindle 11 as described turns freely in the bore 12 in the body 1.

The grooves 19 and 26 are symmetrically and identically disposed in the spindle 11, that is they are of the same form and equally spaced from the respective ends of the spindle. Thus, the spindle is reversible, which materially simplified mechanical handling and assembly.

I claim:

1. A castor comprising a body adapted to be mounted about a vertical mounting axis and moulded with a first integral bearing boss, a wheel moulded with a second integral bearing boss and having an external peripheral groove on said boss, said wheel being rotatably mounted on said body with said first and second integral bearing bosses engaging one within the other in a manner to provide a bearing for the wheel about a rotation axis offset laterally of and inclined to said vertical mounting axis of the body which is further moulded with a spindle bore aligned with said vertical axis, and a mounting spindle located in said spindle bore and engaging in said peripheral groove to locate the wheel axially with respect to the body, said body and said spindle having interengaging formations which locate the spindle axially in the body and provide a snap-in fixing of the spindle in the body moulding.

2. A castor according to claim 1, wherein said interengaging formations comprise an internal integral projection of the body moulding and a peripheral groove in the spindle.

3. A castor according to claim 1, wherein said body is moulded with a hollow internal space open on the side adjacent said wheel, said spindle bore has an inner end which terminates at said hollow space and said internal projection is moulded at said inner end of said spindle mounting bore and projects radially inwardly into that bore.

4. A castor according to claim 1, wherein said first boss acts as a stub axle and engages within the second boss, which is hollow for the purpose, to provide a bearing journal for the wheel.

5. A castor according to claim 4, wherein the external periphery of the second boss provides a bearing journal which runs within a female bearing surface of the body.

6. A castor according to claim 1, wherein the spindle is axially located and rotatably supported in a fixing member which turns freely on the spindle, and the spindle has a "snap-in" fixing in the fixing member also.

7. A castor according to claim 6, wherein in use the vertical load supported by the castor is transmitted directly to the body a thrust face on the body surrounding the spindle being engaged by a thrust face on the fixing member.

8. A castor according to claim 6, wherein the spindle is a length of steel rod and each snap-in fixing is provided by a corresponding peripheral groove in the rod which is engaged by a respective lip or projection in the body or fixing member to provide the fixing.

9. A castor according to claim 8, wherein the grooves are symmetrically disposed in the spindle and equispaced from the ends of the spindle which is accordingly reversible.

10. A castor comprising a body moulding adapted to be mounted about a vertical mounting axis, said body being moulded with a wheel bearing stub shaft and a concentric journal bearing surface surrounding the stub shaft, a wheel moulding rotatably mounted on said body moulding about a rotation axis offset laterally of and inclined to said mounting axis, said wheel being moulded with an integral projecting hollow bearing boss received and taking a bearing between said stub shaft and said concentric journal bearing surface, said body being moulded with a spindle mounting bore aligned with said mounting axis and said bearing boss of the wheel having a peripheral groove with said journal bearing surface cut away in the region of the mounting axis and peripheral groove, and a castor mounting spindle located in said mounting groove in the body and extending through said cut-away region of the journal bearing surface into engagement with said peripheral groove in said integral bearing boss thereby to retain the wheel axially with respect to the body.

11. A castor according to claim 10, wherein said concentric journal bearing surface is formed within an integral sleeve portion of the body moulding which is cut away in the region of a hollow space in the body moulding at the inner end of said spindle mounting bore, the wall of said space providing a stop face for engagement by the inner end of the spindle which extends into said space for engagement with said peripheral groove in said integral bearing boss of the wheel moulding, a projection at said inner end of the spindle mounting bore engaging a recess in said spindle to provide snap-in fixing of the latter in the body moulding.

* * * * *